(12) United States Patent
Budolfsen et al.

(10) Patent No.: US 9,247,753 B2
(45) Date of Patent: Feb. 2, 2016

(54) PREPARATION OF DOUGH OR BAKED PRODUCTS

(71) Applicant: Novozymes A/S, Bagsvaerd (DK)

(72) Inventors: Gitte Budolfsen, Frederiksberg (DK); Luise Christiansen, Copenhagen (DK); Todd Forman, Raleigh, NC (US); Tina Spendler, Herlev (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/964,164

(22) Filed: Aug. 12, 2013

(65) Prior Publication Data

US 2013/0323359 A1    Dec. 5, 2013

Related U.S. Application Data

(63) Continuation of application No. 13/310,011, filed on Dec. 2, 2011, which is a continuation of application No. 12/882,626, filed on Sep. 15, 2010, now abandoned, which is a continuation of application No. 11/738,838, filed on Apr. 23, 2007, now abandoned, which is a continuation of application No. 10/332,164, filed as application No. PCT/DK01/00472 on Jul. 6, 2001, now abandoned.

(60) Provisional application No. 60/217,051, filed on Jul. 10, 2000.

(30) Foreign Application Priority Data

Jul. 6, 2000    (DK) ................................ 2000 01054

(51) Int. Cl.

| A21D 2/00 | (2006.01) |
|---|---|
| A21D 10/00 | (2006.01) |
| A21D 13/00 | (2006.01) |
| C12N 9/16 | (2006.01) |
| A21D 8/04 | (2006.01) |
| C11B 3/00 | (2006.01) |
| C12N 9/18 | (2006.01) |
| C12N 9/20 | (2006.01) |

(52) U.S. Cl.
CPC ............... *A21D 8/042* (2013.01); *C11B 3/003* (2013.01); *C12N 9/16* (2013.01); *C12N 9/18* (2013.01); *C12N 9/20* (2013.01); *C12Y 301/01003* (2013.01); *C12Y 301/01004* (2013.01); *C12Y 301/01026* (2013.01); *C12Y 301/01032* (2013.01)

(58) Field of Classification Search
None
See application file for complete search history.

(56) References Cited

U.S. PATENT DOCUMENTS

| 3,652,397 | A | 3/1972 | Pardun |
|---|---|---|---|
| 5,989,599 | A | 11/1999 | Chimiel |
| 6,127,137 | A | 10/2000 | Hasida et al. |
| 6,146,869 | A | 11/2000 | Harris et al. |

FOREIGN PATENT DOCUMENTS

| EP | 01090244 A1 | 5/1984 |
|---|---|---|
| EP | 0171995 B1 | 2/1991 |
| EP | 0575133 A2 | 12/1993 |
| EP | 0585988 A1 | 3/1994 |
| EP | 0869167 A2 | 10/1998 |
| EP | 1108360 A1 | 6/2001 |
| WO | 9404035 A1 | 3/1994 |
| WO | 9826057 A1 | 6/1998 |
| WO | 9844804 A1 | 10/1998 |
| WO | 9845453 A1 | 10/1998 |
| WO | 9503769 A1 | 10/1999 |
| WO | 0028044 A1 | 5/2000 |
| WO | 0183770 A2 | 11/2001 |
| WO | 0200852 A2 | 1/2002 |

OTHER PUBLICATIONS

Carriere et al, Biochim Biophys Acta, vol. 1376, pp. 417-432 (1998).
Marion et al, Wheat structure, Biotechnology and Functionality, The Proceedings of a Conference Organized by the Royal Society of Chemistry Group, held on Apr. 10-12, 1995 in Reading UK, "Wheat Lipid-Binding ProteinsL Structure and Function", pp. 245-260 (2000).
Marion et al, Interaction: The Key to Cereal Quality, Chapter 6, "Lipids, Lipid-Protein Interactions and the Quality of Baked Cereal Products", pp. 131-167 (1998).
Slides and Transcript of Presentation, Effect and Functionality of Lipases in Dough & Bread Santorini Congress (May 8, 1999).

*Primary Examiner* — Iqbal H Chowdhury
(74) *Attorney, Agent, or Firm* — Kristin J. McNamara

(57) ABSTRACT

The addition to dough of a combination of two lipolytic enzymes with different substrate specificities produces a synergistic effect on the dough or on a baked product made from the dough, particularly a larger loaf volume of the baked product and/or a better shape retention during baking.

4 Claims, No Drawings

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic construct

<400> SEQUENCE: 1

Ser Pro Ile Arg Arg
1               5

PREPARATION OF DOUGH OR BAKED PRODUCTS

CROSS-REFERENCE TO RELATED APPLICATIONS

This application is a continuation of U.S. application Ser. No. 13/310,011 filed on Dec. 2, 2011 (now abandoned), which is a continuation of U.S. Ser. No. 12/882,626 filed on Sep. 15, 2010 (now abandoned), which is a continuation of U.S. application Ser. No. 11/738,838 filed on Apr. 23, 2007 (now abandoned), which is a continuation of U.S. application Ser. No. 10/332,164 filed on Jan. 3, 2003 (now abandoned), which claims priority of 35 U.S.C. 371 national application of PCT/DK01/00472 filed Jul. 6, 2001, which claims priority or the benefit under 35 U.S.C. 119 of Danish application no. PA 2000 01054 filed Jul. 6, 2000 and U.S. provisional application No. 60/217,051 filed Jul. 10, 2000, the contents of which are fully incorporated herein by reference.

SEQUENCE LISTING

Applicants submit herewith a Sequence Listing in the form of a text file.

TECHNICAL FIELD

The present invention relates to methods of preparing a dough or a baked product made from dough by use of lipolytic enzymes, and to compositions for use therein.

BACKGROUND

WO 94/04035, EP 109244, EP 585988, WO 98/26057, WO 98/45453, WO 99/53769, WO 00/32758 and EP 575133 describe the addition of various lipolytic enzymes to dough in the preparation of bread, e.g. enzymes with activities such as triacylglycerol lipase, phospholipase and galactolipase.

SUMMARY OF THE INVENTION

The inventors have found that the addition to dough of a combination of two lipolytic enzymes with different substrate specificities produces a synergistic effect on the dough or on a baked product made from the dough, particularly a larger loaf volume of the baked product and/or a better shape retention during baking.

Accordingly, the invention provides a method of preparing a dough or a baked product made from dough, comprising adding a combination of two lipolytic enzymes to the dough. The invention also provides a composition comprising a combination of two lipolytic enzymes.

The combination may comprise at least two lipolytic enzymes selected from the group consisting of galactolipase, phospholipase and triacylglycerol lipase. Thus, the combination may comprise a galactolipase+a phospholipase, a phospholipase+a triacylglycerol lipase or a triacylglycerol lipase+a galactolipase.

DETAILED DESCRIPTION OF THE INVENTION

Lipolytic Enzyme

The invention uses a combination of lipolytic enzymes, i.e. enzymes which are capable of hydrolyzing carboxylic ester bonds to release carboxylate (EC 3.1.1). The enzyme combination includes at least two of the following three: a galactolipase, a phospholipase and a triacylglycerol lipase, i.e. enzymes predominantly having activity for a galactolipids, a phospholipid, and a triglyceride, respectively. The activities may be determined by any suitable method, e.g. by assays known in the art or described later in this specification.

Galactolipase activity (EC 3.1.1.26), i.e. hydrolytic activity on carboxylic ester bonds in galactolipids such as DGDG (digalactosyl diglyceride). The galactolipase activity (digalactosyl diglyceride hydrolyzing activity or DGDGase activity) may be determined, e.g., by the plate assay in this specification or by the monolayer assay 1 or 2 in WO 2000/32758.

Phospholipase activity (A1 or A2, EC 3.1.1.32 or 3.1.1.4), i.e. hydrolytic activity towards one or both carboxylic ester bonds in phospholipids such as lecithin. The phospholipase activity may be determined by the plate assay in this specification or by an assay WO 2000/32758, e.g. the PHLU, LEU, monolayer or plate assay 1 or 2.

Triacylglycerol lipase activity (EC 3.1.1.3), i.e. hydrolytic activity for carboxylic ester bonds in triglycerides, e.g. 1,3-specific activity, particularly on long-chain triglycerides such as olive oil. The activity on long-chain triglycerides (olive oil) and short-chain triglycerides (tributyrin) may be determined by the SLU and LU methods (described in WO 00/32758), respectively, or by the plate assay described in this specification. The enzyme may have a substrate specificity for hydrolyzing long-chain fatty acyl groups rather than short-chain groups, expressed e.g. as a high ratio of activities on olive oil and tributyrin, e.g. the ratio SLU/LU. Favorably, this may reduce the development of off-odor in dough containing milk lipids such as butter fat. Suitably, this ratio may be above 3.

Each lipolytic enzyme may have a narrow specificity with activity for one of the three substrates and little or no activity for the other two, or it may have a broader specificity with predominant activity for one substrate and less activity for the other two substrates.

A lipolytic enzyme is considered to be a galactolipase if it has a higher activity on galactolipids than on phospholipids and triglycerides. Similarly, it is considered to be a phospholipase or a triacylglycerol lipase if it has a higher activity for that substrate than for the other two. The comparison may be done, e.g., by the plate assay in this specification using the three substrates; the largest clearing zone indicating the predominant activity.

The enzyme combination may comprise three or more lipolytic enzymes, e.g. comprising a galactolipase, a phospholipase and a triacylglycerol lipase.

The enzyme combination may have low activity on partially hydrolyzed lipids such as digalactosyl monoglyceride (DGMG), lysophospholipids (LPL) and mono- and diglycerides (MG, DG). Favorably, this may lead to accumulation of such partially hydrolyzed lipids in the dough and may improve the properties of the dough and/or the baked product.

Sources of Lipolytic Enzymes

The lipolytic enzymes may be prokaryotic, particularly bacterial, e.g. from *Pseudomonas* or *Bacillus*. Alternatively, the lipolytic enzymes may be eukaryotic, e.g. from fungal or animal sources. Fungal lipolytic enzymes may be derived, e.g. from the following genera or species: *Thermomyces*, particularly *T. lanuginosus* (also known as *Humicola lanuginosa*); *Humicola*, particularly *H. insolens*; *Fusarium*, particularly *F. oxysporum*, *F. solani*, and *F. heterosporum*; *Aspergillus*, particularly *A. tubigensis*, *A. niger*, and *A. oryzae*; *Rhizomucor*; *Candida*, particularly *C. antarctica*;

*Penicillium*, particularly *P. camembertii; Rhizopus*, particularly *Rhizopus oryzae*; or *Absidia*.

Some particular examples of lipolytic enzymes follow:

Phospholipase from bee or snake venom or from mammal pancreas, e.g. porcine pancreas.

Phospholipase of microbial origin, e.g. from filamentous fungi, yeast or bacteria, such as the genus or species *Aspergillus, A. niger, Dictyostelium, D. discoideum, Mucor, M. javanicus, M. mucedo, M. subtilissimus, Neurospora, N. crassa, Rhizomucor, R. pusillus, Rhizopus, R. arrhizus, R. japonicus, R. stolonifer, Sclerotinia, S. libertiana, Trichophyton, T. rubrum, Whetzelinia, W. sclerotiorum, Bacillus, B. megaterium, B. subtilis, Citrobacter, C. freundii, Enterobacter, E. aerogenes, E. cloacae Edwardsiella, E. tarda, Erwinia, E. herbicola, Escherichia, E. coli, Klebsiella, K. pneumoniae, Proteus, P. vulgaris, Providencia, P. stuartii, Salmonella, S. typhimurium, Serratia, S. liquefasciens, S. marcescens, Shigella, S. flexneri, Streptomyces, S. violeceoruber, Yersinia*, or *Y. enterocolitica*.

Lipase from *Thermomyces lanuginosus* (*Humicola lanuginosa*) (EP 305216, U.S. Pat. No. 5,869,438).

Lipase/phospholipase from *Fusarium oxysporum* (WO 98/26057).

Lysophospholipases from *Aspergillus niger* and *A. oryzae* (WO 0127251).

Phospholipase A1 from *Aspergillus oryzae* (EP 575133, JP-A 10-155493).

Lysophospholipase from *F. venenatum* (WO 00/28044).

Phospholipase B from *A. oryzae* (U.S. Pat. No. 6,146,869).

Lipase from *A. tubigensis* (WO 9845453).

Lipase from *F. solani* (U.S. Pat. No. 5,990,069).

Lipolytic enzyme from *F. culmorum* (U.S. Pat. No. 5,830,736).

Phospholipase from *Hyphozyma* (U.S. Pat. No. 6,127,137).

Lipolytic enzymes described in PCT/DK 01/00448.

Lipolytic enzymes described in DK PA 2001 00304.

A variant obtained by altering the amino acid sequence a lipolytic enzyme, e.g. one of the above, e.g. as described in WO 2000/32758, particularly Examples 4, 5, 6 and 13, such as variants of lipase from *Thermomyces lanuginosus* (also called *Humicola lanuginosa*).

The lipolytic enzymes may have a temperature optimum in the range of 30-90° C., e.g. 30-70° C.

Synergistic Effect

The combination of the two lipolytic enzymes has a synergistic effect on dough made with the combination or on a baked product made from the dough, particularly improved dough stabilization, i.e. a larger loaf volume of the baked product and/or a better shape retention during baking, particularly in a stressed system, e.g. in the case of over-proofing or over-mixing.

Additionally or alternatively, the synergistic effect on the baked product may include a lower initial firmness and/or a more uniform and fine crumb, improved crumb structure (finer crumb, thinner cell walls, more rounded cells), of the baked product, Additionally or alternatively, there may be a synergistic effect on dough properties, e.g. a less soft dough, higher elasticity, lower extensibility.

Synergy may be determined by making doughs or baked products with addition of the first and the second lipolytic enzyme separately and in combination, and comparing the effects; synergy is indicated when the combination produces a better effect than each enzyme used separately.

The comparison may be made between the combination and each enzyme alone at double dosage (on the basis of enzyme protein or enzyme activity). Thus, synergy may be said to occur if the effect of 0.5 mg of enzyme A+1.0 mg of enzyme B is greater than the effect with 1.0 mg of enzyme A and also greater than the effect with 2.0 mg of enzyme B.

Alternatively, the comparison may be made with equal total enzyme dosages (as pure enzyme protein). If the effect with the combination is greater than with either enzyme alone, this may be taken as an indication of synergy. As an example, synergy may be said to occur if the effect of 0.5 mg of enzyme A+1.0 mg of enzyme B is greater than with 1.5 mg of enzyme A or B alone.

Suitable dosages for the enzymes may typically be found in the range 0.01-10 mg of enzyme protein per kg of flour, particularly 0.1-5 mg/kg, e.g. 0.2-1 mg/kg. Suitable dosages for each of the two enzymes in the combination may be found by first determining a suitable dosage for each enzyme alone (e.g. the optimum dosage, i.e. the dosage producing the greatest effect) and using 30-67% (e.g. 33-50%, particularly 50%) of that dosage for each enzyme in the combination. Again, if the effect with the combination is greater than with either enzyme used separately, this is taken as an indication of synergy.

A lipolytic enzyme with phospholipase activity may be used at a dosage of 200-5000 LEU/kg of flour, e.g. 500-2000 LEU/kg. The LEU activity unit is described in WO 99/53769.

A lipolytic enzyme with triacylglycerol lipase activity may be used at a dosage of 20-1000 LU/kg of flour, particularly 50-500 LU/kg. The LU method is described in WO 2000/32758.

Additional Enzyme

Optionally, an additional enzyme may be used together with the lipolytic enzymes. The additional enzyme may be an amylase, particularly an anti-staling amylase, an amyloglucosidase, a cyclodextrin glucanotransferase, or the additional enzyme may be a peptidase, in particular an exopeptidase, a transglutaminase, a cellulase, a hemicellulase, in particular a pentosanase such as xylanase, a protease, a protein disulfide isomerase, e.g., a protein disulfide isomerase as disclosed in WO 95/00636, a glycosyltransferase, a branching enzyme (1,4-☐-glucan branching enzyme), a 4-☐-glucanotransferase (dextrin glycosyltransferase) or an oxidoreductase, e.g., a peroxidase, a laccase, a glucose oxidase, a pyranose oxidase, a lipoxygenase, an L-amino acid oxidase or a carbohydrate oxidase.

The additional enzyme may be of any origin, including mammalian and plant, and preferably of microbial (bacterial, yeast or fungal) origin and may be obtained by techniques conventionally used in the art.

The amylase may be a fungal or bacterial alpha-amylase, e.g. from *Bacillus*, particularly *B. licheniformis* or *B. amyloliquefaciens*, or from *Aspergillus*, particularly *A. oryzae*, a beta-amylase, e.g. from plant (e.g. soy bean) or from microbial sources (e.g. *Bacillus*).

The xylanase is preferably of microbial origin, e.g. derived from a bacterium or fungus, such as a strain of *Aspergillus*, in particular of *A. aculeatus, A. niger* (cf. WO 91/19782), *A. awamori* (WO 91/18977), or *A. tubigensis* (WO 92/01793), from a strain of *Trichoderma*, e.g. *T. reesei*, or from a strain of *Humicola*, e.g. *H. insolens* (WO 92/17573).

The amyloglucosidase may be from *Aspergillus*, particularly *A. oryzae*.

The glucose oxidase may be a fungal glucose oxidase, particularly from *Aspergillus niger*.

The protease may be a neutral protease from *Bacillus amyloliquefaciens*.

Anti-Staling Amylase

The method or the composition of the invention may include addition of an anti-staling amylase. In particular, a galactolipase and a phospholipase may be used together with an anti-staling amylase, as described in WO 99/53769. The anti-staling amylase is an amylase that is effective in retarding the staling (crumb firming) of baked products, particularly a maltogenic alpha-amylase, e.g. from *Bacillus stearothermophilus* strain NCIB 11837.

Alternatively, the method or composition of the invention may be made without addition of an anti-staling amylase. In particular, a lipase and a phospholipase may be used without addition of an anti-staling amylase or without addition of a maltogenic alpha-amylase.

Composition Comprising Lipolytic Enzymes

The present invention provides a composition comprising a combination of two lipolytic enzymes as described above. The composition may be an enzyme preparation for use as a baking additive. The composition may also comprise flour and may be a dough or a premix.

Enzyme Preparation

The composition may be an enzyme preparation comprising a combination of lipolytic enzymes, for use as a baking additive in the process of the invention. The enzyme preparation may particularly be in the form of a granulate or agglomerated powder, e.g. with a narrow particle size distribution with more than 95% (by weight) of the particles in the range from 25 to 500 μm.

Granulates and agglomerated powders may be prepared by conventional methods, e.g. by spraying the enzymes onto a carrier in a fluid-bed granulator. The carrier may consist of particulate cores having a suitable particle size. The carrier may be soluble or insoluble, e.g. a salt (such as NaCl or sodium sulfate), a sugar (such as sucrose or lactose), a sugar alcohol (such as sorbitol), starch, rice, corn grits, or soy.

The enzyme preparation may also be supplied as a liquid formulation, particularly a stabilized liquid. Liquid enzyme preparations may, for instance, be stabilized by adding a polyol such as propylene glycol, a sugar or sugar alcohol, lactic acid or boric acid according to established methods.

Dough

The dough of the invention generally comprises wheat meal or wheat flour and/or other types of meal, flour or starch such as corn flour, corn starch, rye meal, rye flour, oat flour, oat meal, soy flour, sorghum meal, sorghum flour, potato meal, potato flour or potato starch.

The dough of the invention may be fresh, frozen or par-baked.

The dough of the invention is normally a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may also comprise other conventional dough ingredients, e.g.: proteins, such as milk powder, gluten, and soy; eggs (either whole eggs, egg yolks or egg whites); an oxidant such as ascorbic acid, potassium bromate, potassium iodate, azodicarbonamide (ADA) or ammonium persulfate; an amino acid such as L-cysteine; a sugar; a salt such as sodium chloride, calcium acetate, sodium sulfate or calcium sulfate.

The dough may comprise fat (triglyceride) such as granulated fat or shortening, but the invention is particularly applicable to a dough where less than 1% by weight of fat (triglyceride) is added, and particularly to a dough which is made without addition of fat.

The dough may further comprise an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin.

Pre-Mix

The invention also provides a pre-mix comprising flour together with two lipolytic enzymes as described above. The pre-mix may contain other dough-improving and/or bread-improving additives, e.g. any of the additives, including enzymes, mentioned above.

Materials and Methods

Enzyme Activity Assays

Phospholipase Activity (PHLU)

Phospholipase activity is measured as the release of free fatty acids from lecithin. 500 μl 4% L-alpha-phosphatidylcholine (plant lecithin from Avanti), 5 mM $CaCl_2$ in 50 mM NaOAc, pH 5 is added to 50 μl enzyme solution diluted to an appropriate concentration in water. The samples are incubated for 10 min at 30° C. and the reaction stopped at 95° C. for 5 min prior to centrifugation (5 min at 7000 rpm). Free fatty acids are determined using the NEFA C kit from Wako Chemicals GmbH; 25 μl reaction mixture is added 250 μl Reagent A and incubated 10 min at 37° C. Then 500 μl Reagent B is added and the sample is incubated again, 10 min at 37° C. The absorption is measured at 550 nm. Substrate and enzyme blinds (preheated enzyme samples (10 min at 95° C.)+substrate) are included. Oleic acid is used as a fatty acid standard. 1 PHLU equals the amount of enzyme capable of releasing 1 μmol of free fatty acid/min at these conditions.

Plate Assay for Phospholipase Activity

A) 50 ml 2% agarose in purified water is melted/stirred for 5 minutes and cooled to 60-63° C.

B) 50 ml 2% plant L-alpha-Phosphatidylcholine 95% in 0.2M NaOAc, 10 mM $CaCl_2$, pH 5.5 at 60° C. in 30 min. is blended in 15 sec. with ultrathorax.

Equal volumes of 2% agarose and 2% Lecithin (A and B) are mixed. 250 μl 4 mg/ml crystal violet in purified water is added as indicator. The mixture is poured into appropriate petri dishes (e.g. 30 ml in 14 cm Ø dish), and appropriate holes are made in the agar (3-5 mm) for application of enzyme solution.

The enzyme sample is diluted to a concentration corresponding to $OD_{280}$=0.5 and 10 microliter is applied into holes in the agarose/lecithin-matrix. Plates are incubated at 30° C. and reaction zones in the plates are identified after 20-24 hours incubation, and the size of the clearing zone indicates the phospholipase activity.

Plate Assays for Galactolipase and Triacylglycerol Lipase Activity

Plate assays are carried out as for the phospholipase assay, except that digalactosyl diglyceride (DGDG) or olive oil is used instead of L-alpha-Phosphatidylcholine.

Baking Methods

Sponge Dough

A liquid sponge is prepared by mixing 34.8 parts of water, 60 parts of flour and 1.5 parts of instant yeast, and fermenting for 3 hours at 24° C. A dough is then prepared by mixing the liquid sponge with 22.93 parts of water, 40 parts of flour, 0.5 part of instant yeast, 11.26 parts of 42 high-fructose corn syrup, 0.25 part of calcium propionate, 2 parts of oil and 2 parts of salt, 50 ppm of ascorbic acid 50 parts of wheat flour, 0.5 part of SSL (sodium stearoyl-2-lactylate), 2 parts of salt, 6 parts of sugar and water and ascorbic acid as required.

European Straight Dough Procedure

A dough is prepared by mixing 100 parts (by weight) of wheat flour, 4 parts of yeast, 1.5 parts of salt and 1.5 parts of sugar with water and ascorbic acid as required to reach a suitable dough consistency.

Shape Factor (Shape Retention)

The shape factor is taken as the ratio between the height and diameter of rolls after baking (average of 10 rolls). A higher value indicates a better shape retention.

Dough Softness

Softness is a measure of the degree to which, or ease with which, a dough will compress or resist compression. A sensory evaluation is done by a trained and skilled baker feeling and squeezing the dough. The results are expressed on a scale from 0 (little softness) to 10 (very soft) with the control (dough without enzyme addition) taken as 5.

Dough Extensibility

Extensibility is a measure of the degree by which a dough can be stretched without tearing. A sensory evaluation is done by a trained and skilled baker pulling a piece of kneaded dough (about 30 g) and judging the extensibility. The results are expressed on a scale from 0 (Short/low extensibility) to 10 (long/high extensibility) with the control (dough without enzyme addition) taken as 5.

Dough Elasticity

Elasticity is a measure of the degree to which a dough tends to recover its original shape after release from a deforming force. It is evaluated by rolling a piece of dough (about 30 g) to a size of about 10 cm, and having a trained and skilled baker carefully pulling at opposite ends to judge the resistance and elasticity. The results are expressed on a scale from 0 (low/weak elasticity/recovery) to 10 (high/strong elasticity/recovery) with the control (dough without enzyme addition) taken as 5.

EXAMPLES

Example 1

Synergistic Effect of Phospholipase and Galactolipase on Dough Stabilization

Lipolytic enzyme combinations were tested in a European Straight dough procedure as described above. Fungal alpha-amylase (Fungamyl Super MA, 40 ppm) and an oxidation system (ascorbic acid, 30 ppm) were added to the dough system. Each dough was split into rolls and pan bread. Overproofing (indicating a stressed system) was carried out for the rolls (70 min.) and the pan bread (80 min.).

Combinations with the following lipolytic enzymes were tested: Variant 39 was tested in combination with variant 91 or with *Aspergillus oryzae* phospholipase. Variants 39 and 91 are variants of the *Thermomyces lanuginosus* lipase according to WO 2000/32758.

The combination of variants 91 and 39 was selected because of the high phospholipase activity and the high galactolipase activity, respectively. The *Aspergillus oryzae* phospholipase and variant 39 combination were chosen due to the combination of a pure phospholipase and an enzyme with high DGDG activity. The plate assays described above showed that each enzyme wasx specific with little or no activity for the two other substrates.

The lipolytic enzymes were added according to the table below. The tests with a single enzyme were conducted with a dosage found to be optimum for the enzyme in question, and combinations were tested as indicated, with each enzyme at 33, 50 or 67% of optimal dosage.

| Lipolytic enzyme | Rolls | | Pan bread |
|---|---|---|---|
| | Specific volume (ml/g) | Shape factor | Specific volume (ml/g) |
| Variant 91 (20 LU/kg) | 7.52 | 0.66 | 5.75 |
| Variant 39 (250 LU/kg) | 7.42 | 0.65 | 5.77 |
| Variant 91 (50%) + variant 39 (33%) | 7.57 | 0.66 | 5.94 |

The results demonstrate that the combination of Variant 91 with Variant 39, added at 50% and 33% respectively of optimal dosage, improves the specific volume for both the rolls and the pan bread compared to the each enzyme added separately at optimum dosage.

The results regarding volume and stability improvement from the combination of *Aspergillus oryzae* phospholipase with Variant 39 are listed in the table below.

| Lipolytic enzyme | Rolls | | Pan bread |
|---|---|---|---|
| | Specific volume (ml/g) | Shape factor | Specific volume (ml/g) |
| *A. oryzae* Phospholipase 0.1 mg/kg | 6.27 | 0.57 | 4.96 |
| Variant 39 (250 LU/kg) | 6.40 | 0.60 | 5.18 |
| *A. oryzae* Phospholipase (33%) + variant 39 (67%) | 7.31 | 0.68 | 5.80 |

The combination of *A. oryzae* Phospholipase and Variant 39 at 33% and 67%, respectively, of optimal dosage increases the specific volume considerably compared to each enzyme added separately at optimum dosage. The combination also has a positive contribution to the shape factor of the rolls.

Both the results described above show that the combination of a phospholipase and a galactolipase improves the volume and stability (shape factor) of the rolls and bread, compared to the rolls and bread containing up to thrice the dosages of the enzymes added separately.

Example 2

Synergistic Effect of Triacylglycerol Lipase and Phospholipase on Dough Stabilization A phospholipase A2 from porcine pancreas was tested in combination with a 1,3-specific triacylglycerol lipase from *Thermomyces lanuginosus* in the European straight dough procedure as described above. The results were compared to each enzyme used alone in dosages considered to be optimal. The enzyme combination was made with 50% of optimal dosage of each of the enzymes.

Each dough was split into rolls and pan bread. The rolls were proofed for 70 minutes (over proofing), and the pan bread was proofed for 80 minutes (over proofing). The over proofing was carried out to stress the system in order to test the stabilizing effect of the enzymes.

|  | Rolls | | Pan bread |
| --- | --- | --- | --- |
|  | Sp. Vol (ml/g) | Shape factor | Sp. Vol (ml/g) |
| Phospholipase (3 mg) | 6.24 | 0.56 | 5.60 |
| Triacylglycerol lipase (1000 LU) | 6.43 | 0.58 | 5.43 |
| Phospholipase + triacylglycerol lipase (50%/50%) | 6.88 | 0.60 | 5.93 |

The two enzymes were found to be very specific, i.e. the triacylglycerol lipase has very little activity on phospholipid and galactolipids, and the phospholipase has very little activity on triglycerides and galactolipids.

The results show that when the phospholipase and the triacylglycerol lipase are combined they give a better volume and shape factor than each of the enzyme separately in a stressed system.

Example 3

Synergistic Effect on Dough Properties and Loaf Volume

The combination of Lipase/phospholipase from *Fusarium oxysporum* (FoL) and Variant 6 on dough and bread was evaluated. Variant 6 is a variant of the *Thermomyces lanuginosus* lipase with the following amino acid alterations (SPIRR indicates a peptide extension at the N-terminal, and 270AGGFS indicates a peptide extension at the C-terminal).

Variant 6: SPIRR+G91A+D96W+E99K+G263Q+L264A+I265T+G266D+T267A+L269N+270AGGFS

Loaves were prepared according to the invention by adding Variant 6 (25 LU/kg flour) and FoL (500 LU/kg flour) to the dough. For comparison, loaves were baked without lipolytic enzymes, with FoL alone (1000 LU/kg) or Variant 6 alone (50 LU/kg) which were found to be the optimal dosages for the enzymes. The LU assay method is described in WO 2000/32758.

The standard sponge dough WPB formula was used as described above, with the hydrated distilled MG and SSL eliminated to avoid masking effects on the enzyme. Loaves contained 2% soy oil as well as fungal amylase and pentosanase (Fungamyl Super MA, 50 ppm). The oxidation system was 50 ppm ascorbic acid. In addition to subjective evaluations, crumb softness and elasticity were measured 24 hours after baking. The trial was repeated once.

Dough Evaluations.

Evaluations of the dough at the sheeter are shown below. The dough scores for the two trials were identical.

| Lipolytic enzyme | None | FoL | Variant 6 | FoL + Variant 6 |
| --- | --- | --- | --- | --- |
| Softness | 5.5 | 4.5 | 4.5 | 4.0 |
| Extensibility | 5.0 | 4.5 | 4.5 | 4.0 |
| Elasticity | 5.0 | 5.5 | 5.5 | 6.0 |

The results show that the combination of FoL and Variant 6 yielded dough that was less soft, less extensible and more elastic than either enzyme alone at double dosage.

The specific volume data from the tested loaves are shown below. Reproducibility between the 2 days was high.

| Lipolytic enzyme | None | FoL | Variant 6 | FoL + Variant 6 |
| --- | --- | --- | --- | --- |
| Specific Volume, cc/gram | 6.0 | 6.15 | 6.15 | 6.3 |

The results demonstrate that the combination of two lipolytic enzymes gives a larger loaf volume than either enzyme alone at double dosage.

Example 4

Synergistic Effect on Dough Stabilization

Variant 32 was tested in combination with Variant 13 and Variant 60. The variants are variants of the *Thermomyces lanuginosus* lipase with the following amino acid alterations (where SPIRR indicates a peptide extension at the N-terminal, and 270AGGFS indicates a peptide extension at the C-terminal):

Variant 32: 91A+D96W+E99K+G263Q+L264A+I265T+G266D+T267A+L269N+270AGGFS

Variant 60: G91A+D96W+E99K+G263Q+L264A+I265T+G266S+T267A+L269N+270AGGFS

Variant 13: D96F+G266S

Each combination was tested in a European straight dough procedure, as described above. The results were compared to each enzyme used alone. Lipolytic enzymes were added as shown in the table below. The tests with a single enzyme were conducted with a dosage considered optimum for that enzyme, and the enzyme combinations were tested with each enzyme at 50% of the optimum dosage. The combination of Variant 32 and Variant 13 was also tested with each enzyme at 40% of the optimum dosage, i.e. 20% lower dosage.

Each dough was split into rolls and pan bread. The rolls were proofed for 70 minutes (over proofing), and the pan bread was proofed for 80 minutes (over proofing). The over proofing was carried out to stress the system, in order to test the lipolytic enzymes as stabilizers.

The results from over-proofing are shown below:

| Lipolytic enzyme added | Rolls | | Pan bread |
| --- | --- | --- | --- |
| | Sp. Vol. (ml/g) 70 min | Shape factor 70 min | Sp. Vol. (ml/g) 80 min |
| Variant 32 (200 LU) | 7.78 | 0.67 | 6.16 |
| Variant 13 (500 LU) | 7.24 | 0.66 | 5.69 |
| Variant 60 (100 LU) | 7.02 | 0.67 | 5.69 |
| Variant 32 + Variant 13, 50% | 8.26 | 0.71 | 6.24 |
| Variant 32 + Variant 13, 40% | 8.03 | 0.69 | 6.30 |
| Variant 32 + Variant 60, 50% | 7.87 | 0.69 | 6.39 |

The results show that when the bread is stressed (over-proofed), the combinations of Variant 32 with Variant 13 or Variant 60 clearly give an improved volume and shape compared to each enzyme used alone, particularly Variant 32+Variant 13, even at reduced dosage. The results reveal that when bread is stressed (over proofed), the combinations show a significantly improved effect on volume and shape factor.

Furthermore, it was observed that the combination of Variant 32 and Variant 13 at 40% of optimum dosage provided a more uniform and fine crumb compared to each enzyme used alone.

The invention claimed is:

1. A method for producing a lipolytic enzyme preparation for making baked products, comprising:
   a) determining the substrate specificities of at least two lipolytic enzymes,
   b) selecting two lipolytic enzymes from step a) which are a phospholipase and a galactolipase,
   c) making baked products from doughs with addition of the two lipolytic enzymes of step b) separately and in combination,
   d) determining the loaf volumes or the shape retention of the baked products of step c),
   e) selecting two lipolytic enzymes having a synergistic effect upon the baked products of step c), and
   f) producing the enzyme preparation comprising a combination of the two lipolytic enzymes of step e).

2. The method of claim 1, wherein the phospholipase is phospholipase A1.

3. The method of claim 1, wherein the phospholipase is phospholipase A2.

4. The method of claim 1, wherein the phospholipase is lysophospholipase.

* * * * *